United States Patent
Cohen-Bacrie

(10) Patent No.: US 6,358,206 B1
(45) Date of Patent: Mar. 19, 2002

(54) ULTRASOUND PROCESS FOR THE DETERMINATION OF THE LOCATION OF A PARIETAL SURFACE IN A TISSUE AND OF THE ABSOLUTE RADIUS OF AN ARTERY, AND ULTRASOUND APPARATUS FOR CARRYING OUT SUCH PROCESS

(75) Inventor: Claude Cohen-Bacrie, Paris (FR)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/462,000

(22) Filed: Dec. 15, 1999

(30) Foreign Application Priority Data

Dec. 15, 1998 (EP) .............................. 98403166

(51) Int. Cl.$^7$ ................................ A61B 8/00
(52) U.S. Cl. ...................................... 600/437
(58) Field of Search ................ 600/437, 440, 600/441, 453–456, 463–465; 73/625, 626

(56) References Cited

U.S. PATENT DOCUMENTS 5,197,019 A    3/1993  Delon-Martin et al. ..... 364/563
5,785,654 A  * 7/1998  Iinuma et al. ............... 600/441
5,800,356 A    9/1998  Criton et al. ................ 600/441
6,071,242 A  * 6/2000  Lin ............................. 600/456
6,110,118 A  * 8/2000  Guracar et al. ............. 600/453
6,159,151 A  * 12/2000 Bonnefous .................. 600/440
6,165,128 A  * 12/2000 Cespedes et al. ........... 600/463

FOREIGN PATENT DOCUMENTS

EP         0840239         5/1998       ............. G01S/7/52

* cited by examiner

Primary Examiner—Marvin M. Lateef
Assistant Examiner—Ali M. Imam
(74) Attorney, Agent, or Firm—John F. Vodopia

(57) ABSTRACT

An ultrasound process and apparatus for determining the location of an ultrasonic homogeneity discontinuity called parietal surface situated in a tissue from a radio-frequency signal (y(z)) function of digital depths along an excitation line (Z) crossing the parietal surface. The process and apparatus includes filtering the radio-frequency signal in order to provide a tissue signal (e(z)) representative of tissue scatterers, apart from a radio-frequency excitation signal. Also, filtering the tissue signal (e(z)) in order to provide a variance amplitude signal (S(z)) as a function of the digital depths on the excitation line wherefrom the corresponding parietal surface digital depth is determined. This process is used to estimate an artery radius from the digital depths of the arterial walls on the excitation line.

4 Claims, 3 Drawing Sheets

US 6,358,206 B1

ULTRASOUND PROCESS FOR THE DETERMINATION OF THE LOCATION OF A PARIETAL SURFACE IN A TISSUE AND OF THE ABSOLUTE RADIUS OF AN ARTERY, AND ULTRASOUND APPARATUS FOR CARRYING OUT SUCH PROCESS

BACKGROUND OF THE INVENTION

The invention relates to an ultrasound process for the determination of the location of a local discontinuity of ultrasonic homogeneity forming a parietal surface situated in a tissue, including a step for the acquisition of a radio-frequency signal representing amplitudes of echoes which are returned by tissue scatterers as functions of their digital depths along an excitation line crossing the parietal surface, and are transmitted by a transducer coupled to the tissue and associated with an ultrasound apparatus. The invention also relates to an ultrasound process for the determination of the absolute value of the arterial radius in a tissue from ultrasound frequency signals propagating in the tissue. The invention furthermore relates to an ultrasound apparatus having means to carry out such processes.

The invention is used in the field of manufacture of ultrasound apparatus for clinical examination of arteries so as to assist medical diagnosis of arterial abnormalities without use of invasive means.

For detecting abnormalities of arteries, especially abnormalities of arterial walls, it is helpful to process the ultrasound radio-frequency signals provided by ultrasonic apparatus in order to determine arterial parameters such as the compliance of the arterial walls; this implies accurate determination of the arterial radius variations during a cardiac pulse and, for this purpose, accurate determination of the absolute value of the arterial radius.

An ultrasound signal processing method for determining arterial wall positions in a tissue is already known from the European Patent Application EP 0 840 139 A1. This known method consists in a segmentation of the amplitude signals derived from the ultrasound radio-frequency signals of an ultrasound transducer applied to a tissue region including an artery delimited by its walls. The segmented signals are subjected to a threshold operation in order to separate the pixels which are situated on an excitation line crossing the artery and belong to the internal parietal boundaries of the artery. The determination of the threshold value is based on the difference of gray level between the pixels of the lumen and the pixels of the walls of the artery at these internal parietal boundaries. After the threshold operation, the boundaries are subjected to a smoothing operation using morphological filters. Subsequently, the co-ordinates of the pixels situated on the resultant boundaries and the same excitation line are determined.

This method is used to construct a moving pattern which follows the arterial wall motions during a cardiac cycle in order to assist the diagnosis of abnormalities such as stenosis. As a matter of fact, stenosis or rigid plaques prevent the arterial walls from dilating normally under the influence of the blood pulse. These abnormalities can be diagnosed more easily from the images displayed using the known method, which images show amplified motions of the pattern of the boundaries represented incrusted in an intensity image and tuned to the cardiac cycle.

For this purpose, the known method does not need to provide extremely accurate values of boundary pixel co-ordinates.

Nowadays, diagnoses of vascular diseases and therapeutic choices have to be based on the analysis of the arterial lesion morphology and on the analysis of blood flow. Such analyse imply methods for accurate determination of the arterial wall compliance which require in advance very accurate determination of physiological parameters, and notably determination of extremely accurate values of the arterial radius.

OBJECTS AND SUMMARY OF THE INVENTION

It is an object of the invention to provide a process which can be carried out without invasive means in order to determine the location of a local discontinuity of ultrasonic homogeneity forming a parietal surface situated in a tissue. This object of the invention is achieved by means of an ultrasound process as claimed in claim 1.

It is another object of the invention to provide such a process for determining the location of an artery wall situated in a tissue. This object of the invention is achieved by means of an ultrasound process as claimed in claim 7.

It is another object of the invention to provide the absolute radius value of an artery in a tissue with great accuracy. The problem is that the arteries have mostly small diameters in comparison with other elements of the tissue, and a particular problem is that the wall motions during the cardiac cycle are extremely small and fugitive. So it is very difficult to measure accurately the arterial radius at each instant of the cardiac cycles in order to further determine the radius variations under the influence of blood flow.

This object of the invention is achieved and the problems are solved by means of a process as claimed in claim 8.

This process offers significant advantages because it can be carried out automatically and because it provides very accurate absolute values of the radius of an artery, at a given instant of the cardiac cycle.

An ultrasound apparatus as claimed in claim 9 is provided with a processing system for carrying out the above processes.

The advantage is that the arterial radius can be determined in vivo without using invasive means.

BRIEF DESCRIPTION OF THE DRAWINGS

Specific embodiments of the invention will be described in detail hereafter with reference to accompanying diagrammatic drawings, therein.

DESCRIPTION OF THE PREFERRED EMBODIMENTS

Figure 1:
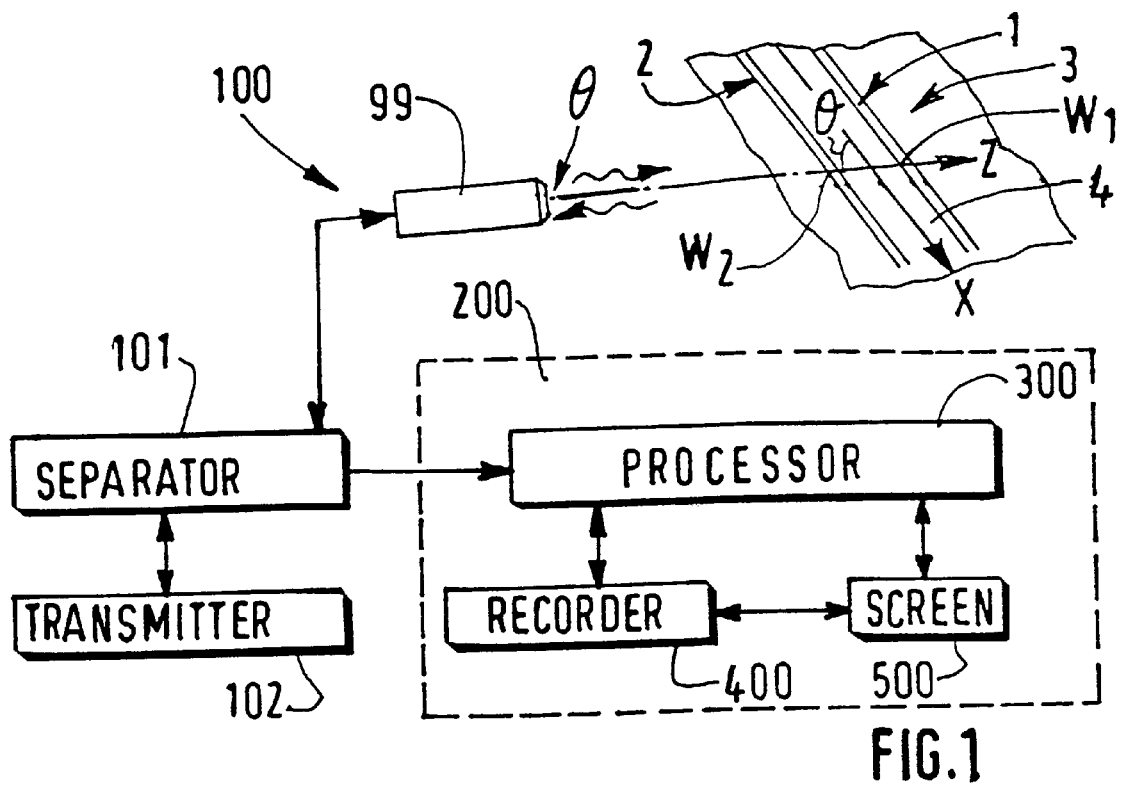
FIG. 1 shows a functional block diagram of an ultrasound apparatus for carrying out ultrasound processes.

Referring to FIG. 1, the invention relates to an ultrasound apparatus 100. This ultrasound apparatus includes an ultrasonic transducer 99 which is connected to a transmitter stage 102, denoted as the transmitter 102, and to a digital processing stage 300. The transducer 99 is in contact with a medium 3 to be observed. The medium 3 contains an artery which is represented by its walls 1, 2 and its lumen 4, having a longitudinal axis X. The transmitter stage 102 includes a sequencer which consists of an oscillator and a frequency divider which controls, with a recurrent period, a generator whose electric excitation signals are applied to the transducer 99. The transducer 99 converts these signals into ultrasound radio-frequency signals which are emitted along an excitation line Z with the recurrent period. The transducer 99 receives, along the same line Z, the echoes returned by obstacles encountered in the medium 3, notably tissue elements, artery walls 1, 2 and blood clusters in the artery lumen. During the examination, it is assumed that the excitation line axis Z encloses an angle* relative to the longitudinal axis X of the artery.

Also referring to FIG. 1, a separating stage denoted as the separator 101, is inserted between a processing stage 200, comprising a processor 300, and the transducer 99 in order to avoid overloading of the stages 102 and 300 by the transmitted signals.

The processor 300 is connected to a display system comprising a screen 500 for displaying ultrasound radio-frequency signals and the signals which are processed by the processor 300. The processor 300 and the display system may also be connected to storage means 400, denoted as the recorder 400, to store the signals for further processing or for ulterior studying. The processor 300 may comprise computing means and internal memory means.

The processor 300, the display system with the screen 500 and the storage means 400 may be constituted by a computer work station 200.

The invention also relates to a process for the determination of the absolute value of the radius of the artery 1, 2, 4 in the medium 3 from the ultrasound radio-frequency signal propagating along the excitation line axis Z. The ultrasound radio-frequency signals as described above propagate according to the M mode of the ultrasound apparatus 100; this is the case when only the echoes along one excitation line within one period are studied. The depths where the echoes are returned by obstacles are digital points denoted $z_i$, where i are indices from 1 to n from an origin called 0, which is generally chosen as the location of the transducer. The digital points $z_i$ are the spatial co-ordinates corresponding to depths of tissue elements, also called scatterers, along the excitation line Z.

As a matter of fact, the process to be described hereafter aims to determine the depth, or co-ordinates, of the central points, denoted $W_1$, $W_2$, in the arterial walls 1, 2, and hence the absolute diameter of the artery along the axis Z related to one recurrent period of the transducer 99. It is of no importance that this axis Z encloses an angle $\theta$ relative to the axis X, because this angle $\theta$ may be determined and taken into account to further calculate the actual cross-sectional diameter of the artery. The steps for the determination of the co-ordinates of the points $W_1$ and $W_2$ are carried out by the processing stage 200.

It is to be noted that the parietal surfaces of the arterial walls in the tissue are seen as discontinuities of ultrasonic homogeneity. For that reason the process described hereafter is also used to determine the co-ordinate on the excitation line of a discontinuity of ultrasonic homogeneity which is referred to as a parietal surface. Said parietal surface may be, for example a tissue lesion.

Figure 2:
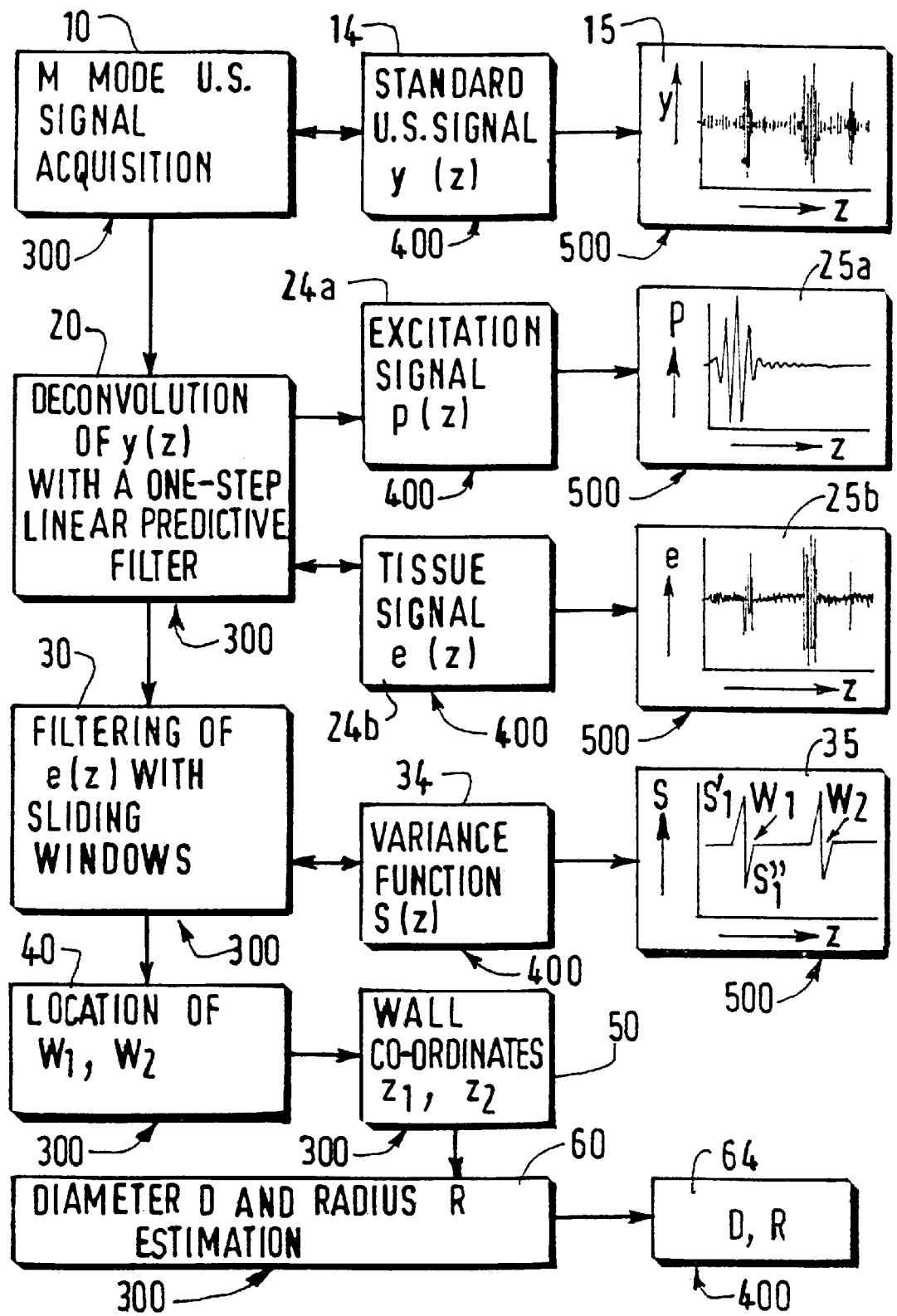
FIG. 2 illustrates the main steps of a process for the determination of an arterial radius.

Referring to FIG. 2, the processing stage 200 performs the following main steps.

A first main step is the acquisition 10 of an ultrasound radio-frequency digital signal y(z) in the M mode, provided by the separating stage 101 of FIG. 1, representing the amplitudes y of the echoes as a function of the digital depths $z_i$ along the excitation line Z. The signal y(z) is shown in box 15 and may be displayed on the screen 500 by means of the display system 400 connected to the processing stage 300 as shown on FIG. 1.

Figure 3:
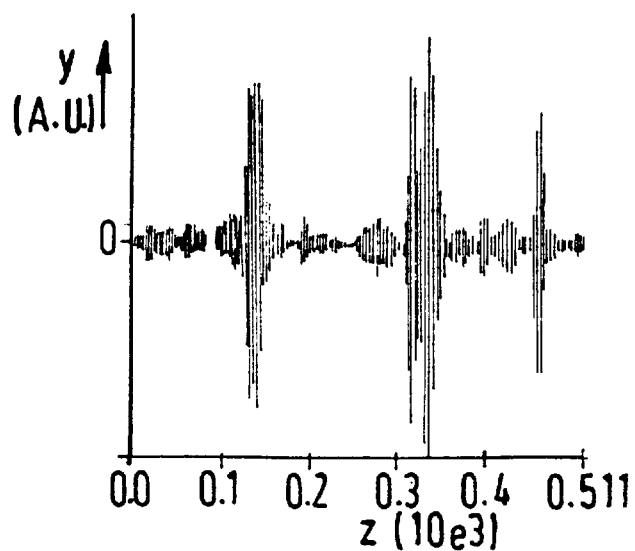
FIG. 3 shows a curve representing an ultrasound signal as a function of depth along an excitation line.

The signal y(z) is also represented in FIG. 3. It shows peaks of amplitude of very different height according to the nature of the scatterers encountered by the excitation line Z. It is to be noted that it is not easy to identify the exact location of the arterial walls from such a curve representing the y(z) signal.

Figure 4:
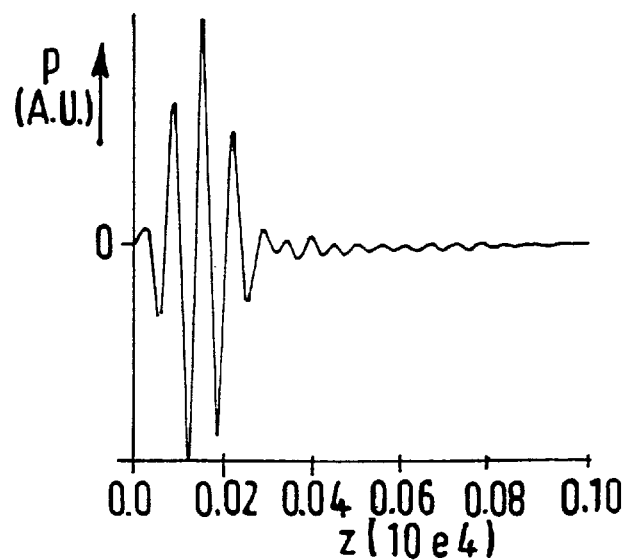
FIG. 4 shows a curve representing the system excitation signal component of the de-convoluted signal.
Figure 5:
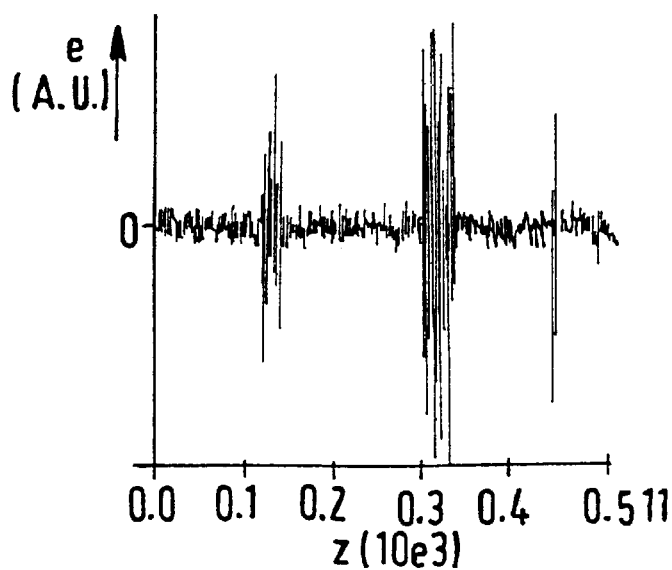
FIG. 5 shows a curve representing the tissue signal component of the de-convoluted signal.

The standard ultrasound signal y(z) of FIG. 3 is also considered to be a convolution signal of a first and a second signal. Referring to FIG. 4, the first signal is the excitation signal p(z) of the ultrasound system 100. Referring to FIG. 5, the second signal represents the density distribution of the scatterers which are elements of the tissue producing the echoes at different digital depths $z_i$ of the axis Z of the excitation line. This second signal is called tissue signal e(z).

Thus, the process also comprises a second main step which is a de-convolution step 20 intended to provide separately the excitation signal p(z) at the output 24a, which is shown in box 25a, and the tissue signal e(z) at the output 24b, which is shown in box 25b. The signals p(z) and e(z) can be displayed on the screen 500 while using the display system 400. Referring to FIG. 5, it is still not easy to localize the artery walls from the peaks of amplitude of the curve representing the tissue signal e(z).

So, the process comprises a third main step 30 for further processing the tissue signal e(z) in order to provide the location of the arterial walls. This processing step 30 is carried out by a filtering operation applied to the tissue signal e(z) in order to provide at the output 34a a signal S(z) representing a variance signal derived from the tissue signal e(z) as a function of the digital depths $z_i$. This variance signal S(z) is shown in box 35 and represented in the FIG. 6. The variance signal S(z) may be displayed on the screen 500 through the display system 400. Said variance signal S(z) shows first parts having a general zero amplitude and second parts having two alternating peaks S', S" between which the amplitude of the variance signal S(z) has a value zero. The locations of the peaks correspond to the locations of the external and internal parietal surfaces, respectively, of one artery wall. It may be elected to calculate the arterial radius, for example from the location and distance of the two internal parietal surfaces of the two walls of an artery. Alternatively, it may be decided to determine the arterial radius from the distance of the central points of the two walls of the artery. One central point of one wall of the artery corresponds to the point of zero amplitude between the two alternating peaks of the variance signal S(z). This point can be matched to one digital co-ordinate $z_i$ on the excitation line axis Z. This co-ordinate $z_i$ is considered to be the depth of the central point of said wall.

So, the process comprises a fourth main step 40 for processing the variance signal S(z). According to the above determination method, the central point $W_1$ of the first arterial wall 1 corresponds to a first depth or co-ordinate $z_1$, and the central point $W_2$ of the second arterial wall 2 corresponds to a second depth or co-ordinate $z_2$. It is assumed that the so called first wall 1 is encountered first by the excitation line Z from the origin 0.

On the basis of the determination 40 of the co-ordinates $z_1$, $z_2$ of the parietal depths of the central points $W_1$, $W_2$ the diameter D and the radius R of the artery can be derived by way of a calculation step 50.

The de-convolution step 20 may be carried out by any means known of those skilled in the art. The de-convolution step, however, is preferably carried out as follows. The de-convolution operation is applied to the standard ultrasound signal y(z), acquired in the M mode, in order to de-convolute this signal y(z) into the first signal p(z), representing the ultrasound system excitation signal, and the second signal e(z) representing the density distribution of the scatterers in the medium 3, which is denoted as the tissue signal e(z).

The processing step 20 implies that the standard ultrasound signal y(z) is actually the result of the convolution between the ultrasound system excitation signal p(z) and a random signal having a Gaussian probability distribution representing the tissue signal e(z).

The de-convolution step 20 is carried out while using a one-step linear predictive filter applied to the samples of the standard ultrasound signal y(z). These samples are the amplitude values of the signal y(z) at each digital depth or co-ordinate on the excitation line axis Z. The co-ordinates are numbered, for example from 1 to n. The one-step predictive filter provides at the step n a sample y(n) which is at a depth $Z_n$, on the excitation line Z and is a function of the number n of samples previously scanned on this excitation line axis Z, with a prediction error e(n).

So, the following formula expresses the result of the one-step linear predictive filter applied to the standard ultrasound signal y(z) at step n:

$$y(n)=a_1 y(n-1)+a_2 y(n-2)+ \ldots +a_n y(0)+e(n) \quad (1)$$

where $a_1, a_2, \ldots, a_n$ are the coefficients of the filter.

This one-step linear predictive filter performs a modelling of the signal y(z) at each step from 1 to n and permits of determining the coefficients $a_1$ to $a_n$. This predictive modelling at step 20 permits of providing this signal e(n) as an estimator of the generating process which provides the signal y(z). The one-step predictive filter thus gives access to the ultrasound system excitation signal p(z) on the one hand and to the tissue signal e(z) on the other hand.

The tissue signal e(z) is constructed on the basis of the digital predictive errors e(n) which are determined at each step from 1 to n in the predictive filter operation step 20 as represented in FIG. 2 in box 25b or in FIG. 5.

The tissue signal e(z) resulting from the de-convolution of the standard ultrasound signal y(z) is modelled as a first Gaussian white noise $e_L$ having a first variance denoted $\sigma^2_L$ whereto there must be added, at particular locations on the excitation line axis Z, a second Gaussian white noise $e_M$ having a second variance $\sigma^2_M$ which is much higher than the first variance $\sigma^2_L$, for example in a ratio of 20 dB. The locations where the second white noise $e_M$ occurs correspond to the artery walls locations. The variances of the white noises model the distribution of the biological elements repartition.

The tissue signal e(z) is thus composed of the first signal $e_L$, having the first variance $\sigma^2_L$ when the echoes of the arterial walls are not present, and is composed of the sum of the first signal $e_L$ and of the second signal $e_M$, said sum having a variance which is the sum of the first and the second variances $\sigma^2_L+\sigma^2_M$, when the echoes of an arterial wall are present.

Figure 7:
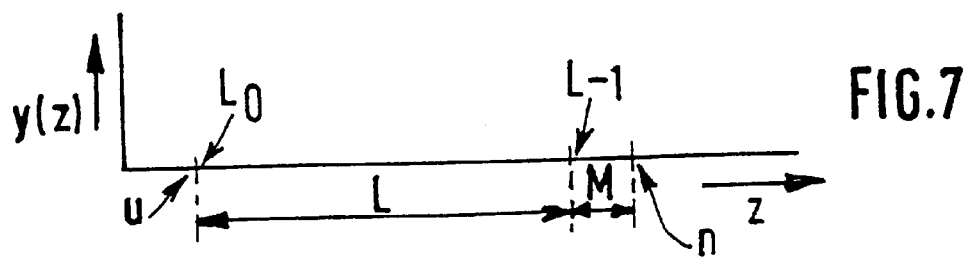
FIG. 7 illustrates the tissue signal filtering step.

Referring to FIG. 2 and to FIG. 7, the next processing step 30 constitutes a detection operation for detecting the presence of walls in the tissue signal e(z). Referring to FIG. 7, this detection step 30 is carried out by a filter constituted by two sliding adjacent windows, denoted as the first window L and the second window M, which are disposed with respect to the excitation line axis Z as shown in FIG. 7. The first window L and the second window M are formed by digital points disposed in the same way as the points of the excitation line axis Z. The number of points of the first window L is denoted as L-1 for simplification and is greater than the number of points of the second window M which is denoted M-1. The respective number L-1 and M-1 of points of the first and second windows are determined on the basis of experience by those skilled in the art. For example, the second window M has a number M of points which is of the order of or inferior to the number of points which is assumed to separate the external parietal surface from the internal parietal surface for one arterial wall. The first window L has a number L-1 of points which is of the order of or inferior to the number of points presumably separating the two internal parietal surfaces of the two walls separated by the lumen of the artery in the cross-sectional view in FIG. 1.

Filtering the tissue signal e(z) while using the two sliding adjacent windows L and M permits of determining the variance of amplitudes in each window, being either the variance of $e_L$ or the variance of $e_L+e_M$. To those skilled in the art the variance is known to be the square standard deviation of amplitudes in each window according to the following two formulae:

$$\sigma_L^2 = \frac{1}{L} \sum_{i=u}^{i=u+L-1} \left( \hat{e}_i - \frac{\sum_i \hat{e}_i}{L} \right)^2 \quad 2a$$

$$\sigma_M^2 = \frac{1}{M} \sum_{j=u+L}^{j=u+L+M-1} \left( \hat{e}_j - \frac{\sum_j \hat{e}_j}{M} \right)^2 \quad 2b$$

From these values $\sigma_L$ and $\sigma_M$ an amplitude $S_u$ is calculated according to the following formula:

$$S_u = \frac{(\sigma_L^2 + \sigma_M^2)\sigma_M^2}{\sigma_L^2} \ln\left( \frac{\sigma_L^2 + \sigma_M^2}{\sigma_M^2} \right) \quad 3$$

where ln is the Neperian logarithm. In these formulae u is the position of the origin $L_0$ of the sliding windows L and M oriented in the same way as the excitation line axis Z.

Figure 6:
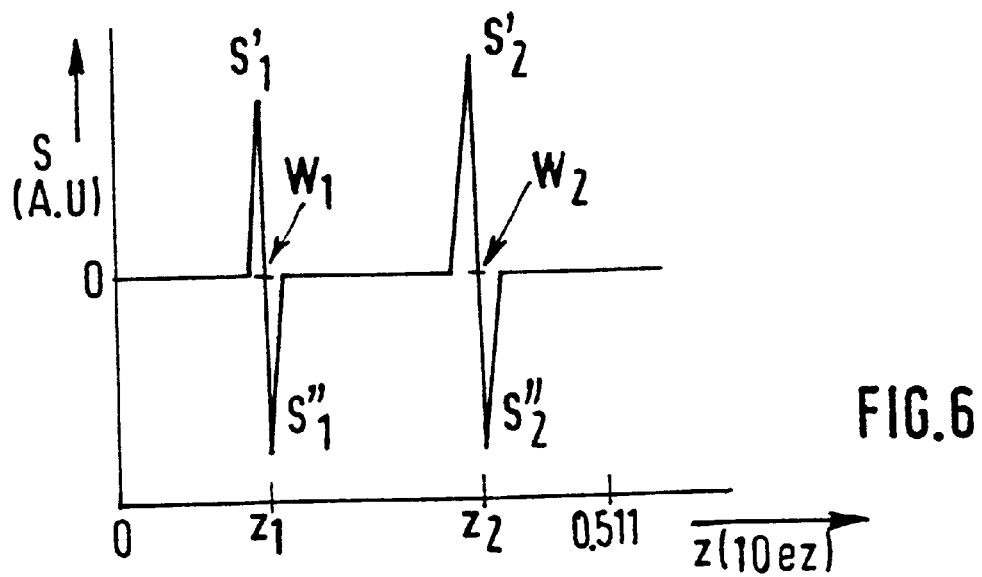
FIG. 6 shows a curve representing a variance signal determined from the tissue signal component filtered so as to determine parietal surface depths on an excitation line.

From the amplitude values $S_u$, determined by sliding the origin $L_0$ of the two sliding adjacent windows from point to point of the excitation line axis Z from point 1 to point n, a variance signal S(z) is constructed as represented in FIG. 6.

Referring to FIG. 2, a processing step 40 permits of identifying the central points $W_1$, $W_2$ of the arterial walls from the variance signal curve S(z) and the processing step 50 permits of determining the corresponding depths or co-ordinates of these central points.

Alternatively, the co-ordinates of the arterial parietal surfaces can be determined.

Calculation means then calculate, in step 60, the diameter D or the radius R from the co-ordinates of these central points $W_1$, $W_2$. These values are stored by storage means, for instance storage means 400, at each period of the ultrasound system in order to provide the variation of the diameter D or of the radius R of the artery for one cross-sectional position related to the position of the excitation line axis Z.

The diameter D and the radius R can be determined by the ultrasound process, using the ultrasound means, for several other cross-sectional positions related to several other excitation line locations with respect to the same artery.

The invention has been described in relation to the determination of arterial wall location along the excitation line. Alternatively, it can be used to determine the location of a simple discontinuity of ultrasound homogeneity in a tissue, called parietal surface, crossed by the excitation line. Its depth on the excitation line is determined from the variance signal S(z) which shows one peak of amplitude arising from a generally zero amplitude signal. Said peak corresponds to the location or depth of said parietal surface, that is to say to the co-ordinate of said parietal surface on the excitation line. This co-ordinate is determined while using the processing steps 10, 20, 30 and 40 which are described with reference to FIG. 2 and are carried out by means of processing means 200, including the processor 300, storage means 400, and the screen 500 associated with the ultrasound apparatus 100.

What is claimed is:

1. An ultrasound process for the determination of the location of a local discontinuity of ultrasonic homogeneity forming a parietal surface situated in a tissue, including a step for the acquisition of a radio-frequency signal (y(z)) representing amplitudes of echoes which are returned by tissue scatterers as functions of their digital depths along an excitation line (Z) crossing the parietal surface, and are transmitted by a transducer coupled to the tissue and associated with an ultrasound apparatus, the process also comprising steps for the determination of the parietal surface digital depth on the excitation line, wherein:

the radio-frequency signal is filtered so as to provide a tissue signal (e(z)) representative of the tissue scatterers, apart from the radio-frequency excitation signal, the tissue signal (e(z)) is filtered so as to provide a variance amplitude signal (S(z)) as a function of the digital depths on the excitation line, on the basis of which the location of the parietal surface is detected and the corresponding parietal surface digital depth on the excitation line is determined, wherein the filtering of the radio-frequency signal is carried out while using a one-step predictive filter, wherein the one-step predictive filtering operation is carried out while scanning the excitation line, in order to provide, at a given depth (n), a sample (y(n)) of the radio-frequency signal which is a linear function on the one hand of the samples previously determined by said scanning which is representative of the radio-frequency excitation signal (p(n)), and on the other hand of a prediction error (e(n)) which is representative of the tissue scatterers.

2. A process as claimed in claim 1, wherein the tissue signal (e(z)) is formed from the prediction errors (e(n)) related to respective digital depths, using a de-convolution operation of the linear samples (y(n)) of the radio-frequency signal (y(z)) determined by said scanning of the excitation line at each digital depth.

3. An ultrasound process for the determination of the location of a local discontinuity of ultrasonic homogeneity forming a parietal surface situated in a tissue, including a step for the acquisition of a radio-frequency signal (y(z)) representing amplitudes of echoes which are returned by tissue scatterers as functions of their digital depths along an excitation line (Z) crossing the parietal surface, and are transmitted by a transducer coupled to the tissue and associated with an ultrasound apparatus, the process also comprising steps for the determination of the parietal surface digital depth on the excitation line, wherein:

the radio-frequency signal is filtered so as to provide a tissue signal (e(z)) representative of the tissue scatterers, apart from the radio-frequency excitation signal, the tissue signal (e(z)) is filtered so as to provide a variance amplitude signal (S(z)) as a function of the digital depths on the excitation line, on the basis of which the location of the parietal surface is detected and the corresponding parietal surface digital depth on the excitation line is determined, wherein the filtering of the tissue signal is carried out by scanning the digital depths on the excitation line while using two sliding adjacent windows (L, M) in order to provide the variances ($\sigma_L$, $\sigma_M$) of amplitudes of the tissue signal (e(z)) in each window at each depth, wherein variance amplitude values ($S_n$) are determined from the variances of amplitude in the sliding windows, at each scanned digital depth, and a variance signal (S(z)) is formed from said variance amplitude values as a function of the digital depths on the excitation line, said variance signal having peaks of amplitude arising from a generally zero amplitude signal, each peak corresponding to the location of a parietal surface from which the parietal surface digital depth on the excitation line is determined.

4. An ultrasound process for the determination of the location of an artery wall in a tissue, wherein an artery is present in the tissue and said artery has two walls which are crossed by the excitation line in a longitudinal plane, each wall having two parietal surfaces, and wherein said variance signal is determined by a process as claimed in claim 6, said variance signal showing two alternating amplitude peaks arising in a generally zero amplitude signal, said alternating peaks corresponding to the presence of the two parietal surfaces of one artery wall (S'1, S"1), and also showing, between said alternating peaks, an intermediate zero amplitude value which represents the central point of said two parietal surfaces, and wherein the digital depth of said central point of the artery wall on the excitation line is determined from said intermediate zero amplitude value.

* * * * *